US010660505B2

(12) United States Patent
Irion et al.

(10) Patent No.: US 10,660,505 B2
(45) Date of Patent: May 26, 2020

(54) METHOD AND APPARATUS FOR EXAMINING THE LIGHT AND/OR IMAGE TRANSMISSION PROPERTIES OF AN ENDOSCOPIC OR EXOSCOPIC SYSTEM

(71) Applicant: Karl Storz SE & Co. KG, Tuttlingen (DE)

(72) Inventors: Klaus-Martin Irion, Emmingen-Liptingen (DE); Omid Abri, Berlin (DE); Stephan Schrader, Berlin (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 197 days.

(21) Appl. No.: 14/755,032

(22) Filed: Jun. 30, 2015

(65) Prior Publication Data

US 2016/0015247 A1    Jan. 21, 2016

(30) Foreign Application Priority Data

Jul. 15, 2014   (DE) .......................... 10 2014 109 888

(51) Int. Cl.
*A61B 1/00*   (2006.01)
*G01N 21/59*  (2006.01)
(Continued)

(52) U.S. Cl.
CPC ...... *A61B 1/00057* (2013.01); *A61B 1/00059* (2013.01); *A61B 1/04* (2013.01);
(Continued)

(58) Field of Classification Search
CPC ... A61B 1/00057; A61B 1/042; A61B 1/0669; A61B 1/0661; A61B 1/04;
(Continued)

(56) References Cited

U.S. PATENT DOCUMENTS 5,434,775 A * 7/1995 Sims ................. G06K 17/0022
                                                  705/7.12
5,820,547 A   10/1998 Strobl et al.
(Continued)

FOREIGN PATENT DOCUMENTS

DE    19638809 A1   4/1998
DE    19855853 A1   6/2000
(Continued)

*Primary Examiner* — Alexandra L Newton
*Assistant Examiner* — Genja M Frankert
(74) *Attorney, Agent, or Firm* — Whitmyer IP Group LLC (57) ABSTRACT

A method for examining the light and/or image transmission properties of an endoscopic or exoscopic system having the components endoscope or exoscope, light carrier, light source and camera, wherein at least the endoscope or exoscope is taken from a first supply quantity of endoscopes or exoscopes and/or at least the light carrier is taken from a second supply quantity of light carriers, wherein the endoscope or exoscope is provided with an identifier and/or the light carrier is provided with an identifier, wherein the identifier or the identifiers contain/s identification data that individualizes the respective endoscope or exoscope and/or the respective light carrier, wherein the components are connected to each other so as to be ready for operation in the form of a current component combination. The method comprises the steps of: capturing the identification data of the endoscope or exoscope and/or the light carrier, capturing at least one transmission parameter of the current component combination, storing the identification data and the captured at least one transmission parameter. Also described is an apparatus for carrying out the method.

29 Claims, 5 Drawing Sheets

(51) Int. Cl.
  *A61B 1/06*  (2006.01)
  *A61B 1/04*  (2006.01)

(52) U.S. Cl.
  CPC ............ *A61B 1/042* (2013.01); *A61B 1/0661* (2013.01); *A61B 1/0669* (2013.01); *G01N 21/59* (2013.01)

(58) Field of Classification Search
  CPC ........ A61B 1/00059; A61B 2560/0223; A61B 90/90; G01N 21/59; G02B 23/26; G02B 23/24; G01M 11/33; G01M 11/30; G06F 19/321; G06F 23/24; G06T 2207/10068; A61M 2205/273
  See application file for complete search history.

(56) References Cited

U.S. PATENT DOCUMENTS

| | | | |
|---|---|---|---|
| 6,361,490 B1 | 3/2002 | Irion et al. | |
| 6,388,742 B1 | 5/2002 | Duckett | |
| 6,436,032 B1 | 8/2002 | Eto et al. | |
| 6,734,958 B1* | 5/2004 | MacKinnon | G01M 11/00 250/228 |
| 7,022,065 B2 | 4/2006 | Leiner et al. | |
| 7,738,940 B2 | 6/2010 | Shoji et al. | |
| 7,875,636 B2 | 1/2011 | Barrow et al. | |
| 8,040,496 B2 | 10/2011 | Leiner et al. | |
| 8,581,972 B2 | 11/2013 | Iwasaki | |
| 2002/0077677 A1 | 6/2002 | Beck et al. | |
| 2002/0137987 A1* | 9/2002 | Watanabe | A61B 1/00105 600/178 |
| 2002/0184122 A1* | 12/2002 | Yamaguchi | G06Q 40/12 705/30 |
| 2003/0105195 A1 | 6/2003 | Holcomb et al. | |
| 2003/0107726 A1 | 6/2003 | Hirt et al. | |
| 2004/0107113 A1* | 6/2004 | Araki | A61B 1/00006 600/118 |
| 2004/0114879 A1 | 6/2004 | Hiereth et al. | |
| 2006/0149126 A1* | 7/2006 | Ertas | A61B 1/00059 600/101 |
| 2006/0183972 A1* | 8/2006 | Tashiro | A61B 1/00041 600/101 |
| 2007/0088193 A1* | 4/2007 | Omori | A61B 1/00059 600/101 |
| 2007/0238923 A1* | 10/2007 | Kubach | G01M 3/26 600/118 |
| 2008/0074492 A1* | 3/2008 | Iwasaki | A61B 1/00059 348/68 |
| 2008/0100699 A1* | 5/2008 | Hibi | A61B 1/00036 348/65 |
| 2008/0225134 A1* | 9/2008 | Amling | A61B 1/00119 348/222.1 |
| 2008/0228031 A1* | 9/2008 | Leiner | A61B 1/00057 600/109 |
| 2009/0032577 A1* | 2/2009 | Aguren | G02B 6/3895 235/375 |
| 2009/0327715 A1* | 12/2009 | Smith | A61B 1/018 713/168 |
| 2011/0087508 A1* | 4/2011 | McConnell | G06Q 10/06 705/7.11 |
| 2011/0140003 A1 | 6/2011 | Beck et al. | |
| 2011/0149057 A1* | 6/2011 | Beck | A61B 1/00057 348/65 |
| 2012/0215066 A1* | 8/2012 | Akiyama | A61B 1/00009 600/109 |
| 2012/0253122 A1* | 10/2012 | Minetoma | A61B 1/00057 600/109 |
| 2013/0150668 A1* | 6/2013 | Kanno | A61B 1/00059 600/109 |
| 2013/0208106 A1* | 8/2013 | De Braak | G01M 11/00 348/130 |
| 2015/0119639 A1* | 4/2015 | Ebata | A61B 1/00059 600/103 |
| 2016/0000306 A1* | 1/2016 | Takayama | G02B 23/2484 600/109 |
| 2017/0085851 A1* | 3/2017 | Honda | A61B 1/04 |
| 2017/0135558 A1* | 5/2017 | Choi | A61B 1/00057 |

FOREIGN PATENT DOCUMENTS

| | | |
|---|---|---|
| DE | 10001289 C1 | 10/2001 |
| DE | 10245140 B4 | 10/2005 |
| DE | 60306309 T2 | 11/2006 |
| EP | 1187496 A1 | 3/2002 |
| EP | 2306750 A1 | 4/2011 |
| EP | 2335556 A1 | 6/2011 |
| EP | 2335557 A1 | 6/2011 |

* cited by examiner

| Examination No. | Endoscope | Light carrier | Light source | Camera | Intensity |
|---|---|---|---|---|---|
| 1 | E1 | L1 | LQ1 | K1 | 0.720 |
| 2 | E2 | L2 | LQ1 | K1 | 0.800 |
| 3 | E3 | L3 | LQ1 | K1 | 0.810 |
| 4 | E4 | L4 | LQ1 | K1 | 0.790 |
| 5 | E5 | L5 | LQ1 | K1 | 0.730 |
| 6 | E1 | L2 | LQ1 | K1 | 0.700 |
| 7 | E2 | L3 | LQ1 | K1 | 0.820 |
| 8 | E3 | L4 | LQ1 | K1 | 0.810 |
| 9 | E4 | L5 | LQ1 | K1 | 0.710 |
| 10 | E5 | L1 | LQ1 | K1 | 0.850 |
| 11 | E1 | L3 | LQ1 | K1 | 0.680 |
| 12 | E2 | L4 | LQ1 | K1 | 0.710 |
| 13 | E3 | L5 | LQ1 | K1 | 0.820 |
| 14 | E4 | L1 | LQ1 | K1 | 0.780 |
| 15 | E5 | L2 | LQ1 | K1 | 0.810 |
| 16 | E1 | L4 | LQ1 | K1 | 0.730 |
| 17 | E2 | L5 | LQ1 | K1 | 0.680 |
| 18 | E3 | L1 | LQ1 | K1 | 0.750 |
| 19 | E4 | L2 | LQ1 | K1 | 0.810 |
| 20 | E5 | L3 | LQ1 | K1 | 0.820 |
| 21 | E1 | L5 | LQ1 | K1 | 0.670 |
| 22 | E2 | L1 | LQ1 | K1 | 0.830 |
| 23 | E3 | L2 | LQ1 | K1 | 0.800 |
| 24 | E4 | L3 | LQ1 | K1 | 0.800 |
| 25 | E5 | L4 | LQ1 | K1 | 0.810 |

Fig. 7

| Components identification | Measurement 1 | Measurement 2 | Measurement 3 | Measurement 4 | Measurement 5 | Average value |
|---|---|---|---|---|---|---|
| E1 | 0.720 | 0.700 | 0.680 | 0.730 | 0.670 | 0.700 |
| E2 | 0.830 | 0.800 | 0.820 | 0.710 | 0.680 | 0.768 |
| E3 | 0.750 | 0.800 | 0.810 | 0.810 | 0.820 | 0.798 |
| E4 | 0.780 | 0.810 | 0.800 | 0.790 | 0.710 | 0.778 |
| E5 | 0.850 | 0.810 | 0.820 | 0.810 | 0.730 | 0.804 |
| L1 | 0.720 | 0.830 | 0.750 | 0.780 | 0.850 | 0.786 |
| L2 | 0.700 | 0.800 | 0.800 | 0.810 | 0.810 | 0.784 |
| L3 | 0.680 | 0.820 | 0.810 | 0.00 | 0.820 | 0.786 |
| L4 | 0.730 | 0.710 | 0.810 | 0.790 | 0.810 | 0.770 |
| L5 | 0.670 | 0.680 | 0.820 | 0.710 | 0.730 | 0.722 |

Fig. 8

METHOD AND APPARATUS FOR EXAMINING THE LIGHT AND/OR IMAGE TRANSMISSION PROPERTIES OF AN ENDOSCOPIC OR EXOSCOPIC SYSTEM

CROSS REFERENCE TO RELATED APPLICATION

The present application claims priority of German patent application filed on Jul. 15, 2014, the contents of which is incorporated herein by reference.

BACKGROUND OF THE INVENTION

The invention relates to a method for examining the light and/or image transmission properties of an endoscopic or exoscopic system.

The invention furthermore relates to an apparatus for examining the light and/or image transmission properties of an endoscopic or exoscopic system.

Endoscopic systems are utilized in surgical procedures, in particular in minimally invasive surgery. In general, an endoscopic system has the components endoscope, light carrier, light source and camera, and possibly further components, such as for example a monitor for representing the endoscopic image. Exoscopic systems are also utilized in surgical procedures, but in open surgery. In general, an exoscopic system has the components exoscope, light carrier, light source and camera, and possibly further components as indicated above relating to the endoscopic systems. The invention will be described below for the sake of simplicity with reference to endoscopic systems, although it is to be appreciated that the following text also applies to exoscopic systems.

Within the meaning of the present invention, the endoscope may be a rigid or flexible endoscope. The endoscope, in typical construction, can have image transmission optics in its shaft and an eyepiece at the proximal end of the shaft. In this case, the imager and the objective of the camera are connected to the eyepiece by a camera head. The endoscope, however, can also be a video endoscope, in which the imager and the objective of the camera are integrated in the endoscope, for example in the distal end of the endoscope shaft. In this case, the eyepiece at the proximal end of the endoscope is omitted, and the endoscope and camera are in part merged into a single component. In general, a camera control unit also belongs to the camera. The light carrier is typically a light-guide cable which is connected at one end to the light source and at the other end to the endoscope. For endoscopes having directly coupled light carriers, the endoscope and light carrier are in part merged into a single component. The endoscope can, however, also include the light source, the light carrier and the camera as integrated parts.

In order to determine the operational capability of an endoscopic system for surgical treatment, the light and image transmission properties of the endoscopic system must be examined regularly.

To examine the light and image transmission properties of an endoscope, numerous approaches have already been proposed, for example in U.S. Pat. No. 5,820,547 A, DE 100 01 289 C1, U.S. Pat. No. 6,388,742 B1, EP 1 187 496 B1, U.S. Pat. No. 6,734,958 B1, U.S. Pat. No. 7,875,636 B2, U.S. Pat. No. 7,022,065 B2, U.S. Pat. No. 8,040,496 B2. The examination apparatuses described in said documents are indeed suitable for determining the light and/or image transmission properties of endoscopes, but owing to their complicated construction, said apparatuses come with disadvantages. They are relatively complex examination structures which are not suitable for examining an endoscopic system in the operating room and in particular cannot be used under sterile conditions.

Moreover, examination apparatuses and methods for ascertaining the properties of endoscopes for more complex endoscopic methods, such as for example for fluorescence endoscopy, are known, for example in DE 196 38 809 C2, DE 198 55 853 B4, EP 2 306 750 A1, EP 2 335 556 A1, EP 2 335 557 A1. Some of said apparatuses can be used under sterile conditions, if the measurement target used for the examination is designed to be able to be sterilized or autoclaved.

The apparatuses and methods disclosed in EP 2 335 556 A1 and EP 2 335 557 A1 allow the use of standard endoscopes for white light endoscopy in addition to endoscopes for fluorescence endoscopy. Here, the examination complexity is relatively low because the endoscopic camera is used as the measurement sensor such that the examination structure requires only a reflection measurement target and no other active measurement sensor. EP 2 335 556 A1 furthermore describes that the result of the examination method of the endoscopic system with respect to functionality or with respect to another property of the endoscopic system, and possibly the result of a subsequent or previous examination of the patient using the endoscopic system are stored in a database.

The disadvantage pertaining to the previously mentioned examination methods and apparatuses is that the examination allows merely knowledge regarding the endoscopic system as a whole (endoscope, light guide, light source, camera) to be gained. In the case of an error, more in-depth examinations on the components level must be carried out. Another disadvantage is that the measurement target must always also be sterilized for use in a sterile area.

DE 603 06 309 T2 describes a system and a method for providing information relating to an endoscope, wherein the system comprises a history information acquisition unit, which acquires an item of information about the use history of an endoscope, an estimation unit which carries out an estimation of a long-term change in the endoscope from first use to the current time on the basis of the acquired information, and a display unit which displays the result of the estimation over a rate of long-term change, which is preset for the endoscope. This system and this method can be used to estimate the quality and performance of an endoscope merely on the basis of empirical values in long-term use. However, no exact statement relating to the current operational capability of the endoscope or indeed of the endoscopic system as a whole can be made therewith. This can be reliably ensured only by an examination that is based on measurement.

In addition, clinicians demand to be able to examine the functionality of an endoscopic system in the operating room and if possible directly before the operation, i.e. under sterile conditions, without the measurement target used in the examination also having to be autoclaved in each case. It should be possible for the operating room personnel to carry out the quality test simply and quickly.

It should also be possible to obtain not only knowledge relating to the current endoscopic system as a whole, but also information relating to the state of at least those components that, owing to reconditioning steps such as sterilization and autoclaving, degrade over time. For example, the light transmittance of the light fibres inside the light carrier and in the endoscope decreases on account of the extreme stresses inside the autoclave over a multiplicity of reconditioning cycles.

Owing to the necessary reconditioning and the multiplicity of daily operations, clinics nowadays have a relatively large number of endoscopes and light guides so as to be able to guarantee an undisturbed operation process and optimum use of the operating room without downtimes owing to reconditioning. Moreover, many clinics also reprocess the camera heads with the image recorder and the objective of the camera by way of autoclaving, such that such clinics also posses a certain number of camera heads. A clinic can likewise have multiple light sources.

Accordingly, various component combinations, in particular endoscope/light carrier combinations, are used statistically over time. For a simple examination of a current component combination as a whole in terms of its quality of light and/or image transmission properties, it has hitherto been impossible to make statements relating to the performance of the individual components without the need to examine the components individually.

SUMMARY OF THE INVENTION

It is an object to provide a method and/or an apparatus enabling a quality test of the endoscopic or exoscopic system as a whole which can be carried out as quickly as possible.

Further, it is an object to provide a method and/or an apparatus enabling a quality test of the endoscopic or exoscopic system as a whole which can be carried out without undue complexity in terms of time or utilization under sterile conditions.

Further, it is an object to provide a method and/or an apparatus enabling a quality test of the endoscopic or exoscopic system, with which it is possible owing to the examination of the endoscopic or exoscopic system as a whole, to also gain knowledge relating to the performance of specific individual components.

According to an aspect of the invention, a method is provided, comprising providing an endoscopic or exoscopic system having the components endoscope or exoscope, light carrier, light source and camera. The endoscope or exoscope is taken from a first supply quantity of endoscopes or exoscopes, wherein the endoscope or exoscope is provided with an endoscope or exoscope identifier containing endoscope or exoscope identification data individualizing the endoscope or exoscope; and/or the light carrier is taken from a second supply quantity of light carriers, wherein the light carrier is provided with a light carrier identifier containing light carrier identification data individualizing the light carrier. The endoscope, the light carrier, the light source and the camera are connected to each other so as to be ready for operation in the form of a current component combination. For examining the light transmission properties and/or image transmission properties of the endoscopic or exoscopic system, the endoscope or exoscope identification data and/or the light carrier identification data is/are captured, a transmission parameter of the current component combination is captured, the endoscope or exoscope identification data and/or the light carrier identification data are stored. Further, the captured transmission parameter is stored.

According to another aspect of the invention, an apparatus is provided, comprising an endoscopic or exoscopic system having the components: endoscope or exoscope, light carrier, light source and camera. The endoscope or exoscope is taken from a first supply quantity of endoscopes or exoscopes, wherein the endoscope or exoscope is provided with an endoscope or exoscope identifier containing endoscope or exoscope identification data individualizing the endoscope or exoscope; and/or the light carrier is taken from a second supply quantity of light carriers, wherein the light carrier is provided with a light carrier identifier containing light carrier identification data individualizing the light carrier. The endoscope, the light carrier, the light source and the camera are connected to each other so as to be ready for operation in the form of a current component combination. For examining the light and/or image transmission properties of an endoscopic or exoscopic system, the apparatus comprises an identification unit which captures the endoscope or exoscope identification data and/or the light carrier identification data, a measurement system that captures a transmission parameter of the current component combination, and a computer unit to which the measurement system and the identification unit are connected and which has a memory unit for storing the endoscope or exoscope identification data and/or the light carrier identification data and for storing the captured transmission parameter.

What is essential in the method of the invention and the apparatus according to the invention is that the endoscopes (the same is true in the case of exoscopes, which will not always be explicitly mentioned below) and/or light carriers present in a clinic, preferably both the endoscopes and the light carriers, are provided with an identifier which allows unique identification, for example by way of the article or serial number, of the respective endoscope and/or the respective light carrier. The identifiers can preferably be read contactlessly. What is essential in the method according to the invention and the apparatus according to the invention is that, when examining a current component combination, the identification data contained in the identifiers of the current endoscope and/or of the current light carrier is captured. During the examination, the measurement system captures at least one transmission parameter of the current component combination as a whole, wherein the transmission parameter is for example the light intensity of the light emitted by the endoscope, or the image brightness of the endoscopic image captured by the camera, or spectral light and/or imaging information. The at least one captured transmission parameter is then, together with the identification data of the endoscope and/or light carrier, stored in the preferably central computer unit. By connecting the measurement system and the identification unit to the computer unit, the performance of the examination is automatic and can be carried out without much manipulation complexity in a very short period of time, in particular before the current component combination is used in a surgical procedure. During the examination, it is preferably moreover possible for a recorded test image of a measurement target to be captured by the camera, which test image is represented for visual monitoring on a monitor and is also stored with the identification data and the captured transmission parameter likewise in the computer unit.

According to the invention, a current component combination as a whole is thus examined in terms of its quality of the light and/or image transmission properties, wherein for each examination of a component combination, the measurement values of the at least one transmission parameter and the identification data at least of the endoscope and/or at least of the light carrier are stored. This opens up the possibility to deduce, by way of a statistical evaluation after a corresponding number of examinations of various component combinations, the performance of specific individual components, in particular of specific endoscopes and/or specific light carriers, without having to examine said components individually. In other words, after a certain number of examinations, which by themselves only contain a statement relating to the performance of the endoscopic system as a whole, can be used to deduce the performance of individual components.

Preferably, a timestamp is also stored with each examination.

In order to examine as quickly as possible the operational capability of the current component combination, in particular before an immediate use of a current component combination in a surgical procedure, one preferred embodiment of the method provides for the ascertainment of the currently captured transmission parameter with respect to the operational capability of the current component combination for use in a surgical procedure, wherein preferably the result of this evaluation is likewise stored in the computer unit. A particularly simple evaluation according to one further preferred embodiment consists of the currently captured transmission parameter being compared to a nominal value. The result of the evaluation can be displayed for the operating room personnel carrying out the examination on a monitor by way of a traffic light representation (red/amber/green).

In the apparatus according to the invention, accordingly the computer unit preferably has an evaluation unit which evaluates the currently captured transmission parameter so as to ascertain the operational capability of the current component combination for use in a surgical procedure, wherein the evaluation unit preferably compares the currently captured transmission parameter to a nominal value.

The "evaluation unit" and the "memory unit", as used above and below, can be in the form of software and/or hardware.

Furthermore, the components of the electronic devices light source and camera of the endoscopic/exoscopic system also preferably have identifiers containing identification data, for example article and serial number, which is stored for example in a memory element of the light source or of the camera inside the device, in the latter case for example in the camera monitoring unit. According to a further preferred embodiment of the method, the identification data of the light source or the camera are additionally readout. In addition or alternatively, this embodiment of the method additionally provides for operating parameters of the light source and/or the camera to be also readout, with such operating parameters for the light source being, for example, the set output and for the camera being, for example, the set zoom and/or set focus and/or corresponding exposure or amplification parameters.

In this context, provision is furthermore made for the operating parameters of the camera and/or the light source to be set, preferably via the computer unit, for the examination of the current component combination.

In this context it is important or at least advantageous with respect to the informative value of the examination of the light and/or image transmission properties of the current component combination that, during each examination, the zoom and focus always have the same settings at the camera lens, since only in that case a constant transmittance (ratio of incident light to intensity of the electrical signal of the camera) can be assumed. In the case of a motorized zoom and focus setting, preferably always the same setting for zoom and focus are carried out for the respective examination, for example using a central system, for example a bus-assisted controller.

Accordingly, in the apparatus, preferably the current camera and/or the current light source are networked with the computer unit such that identification data and/or operating parameters of the camera and/or the light source can be readout into the computer, and any operating parameters can be set via the computer unit.

If the camera of the current component combination does not permit motorized zoom and focus settings, but focus and zoom can only be set manually, it is advantageous according to a further embodiment of the method if a current setting of an operating parameter (in particular zoom and/or focus) of the camera of the current component combination is ascertained by analyzing the image provided by the current component combination. The images of endoscopes generally have a centric circle section, the size of which is dependent on the zoom factor set. On the basis of this, it is therefore possible, knowing the endoscope and camera type, to determine the magnification factor set at the time of the examination using an image analysis.

Correspondingly, in the apparatus, the computer unit preferably has an image analysis device or is connected to one.

In a further preferred embodiment of the method, stored captured transmission parameters, which come from examinations, carried out at time intervals, of the light and/or image transmission properties of different component combinations are evaluated so as to deduce the performance of individual components of the endoscopic or exoscopic system.

In the apparatus, to this end preferably a sequence of transmission parameters, captured at time intervals, of different component combinations is stored in the memory unit, wherein a program is available that evaluates the stored transmission parameters in terms of the performance of individual components.

What is advantageous here is that on the basis of this statistical evaluation, the weakest components can be selected. After a certain number of initial examinations, it will thus be possible to deduce, from the various component combinations, the performance of individual components. If the camera and light source in an operating room are identical for each operation, only the respective endoscope and the respective light carrier change. If, for example, the transmission quality of a specific light carrier is significantly reduced, this will lead in all component combinations in which said light carrier is used or was used to a systemic deterioration of the entire transmission quality. With the increase in the number of examinations of component combinations, in which said light carrier is used or was used, the result will gain increasing statistical support. In this way, it is thus advantageously possible to ascertain poor-quality components without carrying out an examination of the individual components, which means a significant time saving in the examination and a significantly reduced manipulation complexity.

The program can be configured as software or as programmed hardware. The program is for example stored in the central computer unit.

In this context, it is furthermore preferred if the above-mentioned evaluation is carried out with a weighting such that stored transmission parameters that were captured earlier have a lower weighting than stored transmission parameters which are captured later, or are not taken into consideration.

Accordingly, in the apparatus, the program preferably contains an algorithm which in the evaluation of the transmission parameters does not take into consideration transmission parameters that were captured earlier or gives transmission parameters that were captured earlier a lower weighting than transmission parameters that were captured later.

According to the previously mentioned embodiments, the statistical evaluation of the temporally sequentially recorded transmission parameters of different component combinations is carried out according to the principle of the "limited memory" or according to the principle of "diminishing memory". This measure advantageously takes account of the degradation of individual components that increases over time, in particular of endoscopes and light carriers. If examinations or measurements which were taken earlier, and in which a specific component still showed good performance, were to have the same weighting as examinations or measurements which were carried out more recently or as the current examination measurement, a current poor performance of this component would not be sufficiently detectable. The advantage of the previously mentioned measure, on the other hand, is that even spontaneous deteriorations in the transmission properties of individual components can be reliably ascertained. In an evaluation algorithm with "limited memory", examinations or measurements taken much earlier are no longer taken into consideration at all, and in an evaluation algorithm with "a memory diminishing over time", examinations or measurements taken increasingly earlier are taken into consideration in the evaluation with decreasing weighting.

In a further preferred embodiment of the method, the examination of the current component combination is carried out immediately before the use thereof in a surgical procedure, with a measurement target and/or a measurement sensor being used which is connected to the endoscope.

The examination of the current component combination immediately before use in a surgical procedure is made possible by the examination being able to be carried out according to the invention quickly and simply, and also has the advantage that up to the use of the endoscopic system in a surgical procedure, no deterioration of the system is expected.

In addition or alternatively, in the method, provision is preferably made for the examination of the current component combination to be carried out during the use thereof in a surgical procedure, wherein an area of tissue or an instrument at the intracorporeal site is used as the measurement target.

While in the examination before or after use of the current component combination in a surgical procedure an extra-corporeal measurement target is used, which is connected to the endoscope, in an examination intracorporeal tissue surfaces or instrument areas, such as for example the inner surface of the trocar sleeve, through which the endoscope is inserted into the body, are used during a surgical procedure as measurement target.

In this context it is preferred if a multiplicity of individual examinations are carried out automatically during the surgical procedure, and wherein at least those results from individual examinations are stored that represent a poor-quality state of the current component combination.

To this end, preferably the incidence of occurrence of the captured poor-quality states is captured.

It is possible to deduce the performance of the endoscopic system from the multiplicity of individual examinations and from the occurrence probability of insufficient illumination conditions, for example if despite maximum output power from the light source, maximum amplification and exposure time of the camera only a minimum image intensity or an image intensity under a nominal value can be observed in a defined area of interest about the centre of the image.

In a further preferred embodiment of the apparatus, the computer unit transmits the captured identification data, transmission parameters and possibly operating parameters to a remote computer unit for evaluation therein.

The advantage here is that the analysis of the examinations can be carried out in the manner of remote servicing, for example by a service provider, for example by the manufacturer of endoscopic systems that detects, from the analysis remote from the clinic, the weakest components in the endoscopic transmission chain and possibly makes a prediction relating to the sufficient nominal values not being met. This service provider is then able to inform the clinic about vulnerabilities early and to provide corresponding replacement systems.

In a further preferred embodiment of the apparatus, the measurement system has one or more coupling openings for coupling the endoscope/exoscope and/or the light guide.

If the measurement system has a plurality of coupling or input openings, the advantage is that, in addition to the endoscope tip, it is also possible to insert the distal end of the light carrier. If, in a current examination of the component combination as a whole, a significantly poor total transmission is established, the transmission section can additionally be surveyed without an endoscope so as to obtain more exact deductions relating to the partial system of light guide and light source. The utilization complexity is here not significantly increased by the plurality of coupling openings.

The measurement system preferably has a measurement target (for reflecting the light emitted by the endoscope/exoscope and/or for imaging by the endoscope/exoscope) and/or at least one measurement sensor.

What is particularly preferred is if the measurement system has both a measurement target and also at least one measurement sensor, with the advantage that, using the at least one additional measurement sensor, it is possible to assess the partial system of light source, light carrier and light transmission toward the distal end in the endoscope separately and at the same time.

The measurement system preferably has a measurement adapter, via which the current endoscope/exoscope can be coupled to the measurement system such that the distance of a distal end of the endoscope/exoscope to the measurement target is well-defined.

The measurement adapter can be equipped with or without a transparent membrane which for one defines the distance between the endoscope and the measurement target and, owing to the sterile design, protects the cleaned endoscope against premature contamination. Furthermore, the measurement adapter with the measurement target and with or without a transparent membrane can be configured as a sterile disposable product.

In a further preferred embodiment, the identifiers (of the endoscope and/or of the light carrier) and the identification unit cooperate contactlessly, for example using RFID technology or optically or via barcode and barcode reader.

The identification unit reading the identifiers is preferably integrated in the measurement system, for example in the above-mentioned measurement adapter, to which the endoscope and/or the light carrier can be connected.

The at least one transmission parameter captured during an examination is preferably a light intensity of the light emitted by the current endoscope and/or the signal strength or the image brightness of the image captured by the camera.

Further advantages and features can be gathered from the following description and the attached drawing.

It is to be appreciated that the previously mentioned features and the features still to be explained below can be used not only in the respectively stated combination, but also in other combinations or alone without departing from the scope of the present invention.

BRIEF DESCRIPTION OF THE DRAWINGS

Exemplary embodiments of the invention will be described in more detail below with reference to the drawing, in which:

FIGS. 4a) and b) in each case show a further exemplary embodiment of a measurement adapter for use in the measurement system in FIG. 2;

DESCRIPTION OF PREFERRED EXEMPLARY EMBODIMENTS

Figure 1:
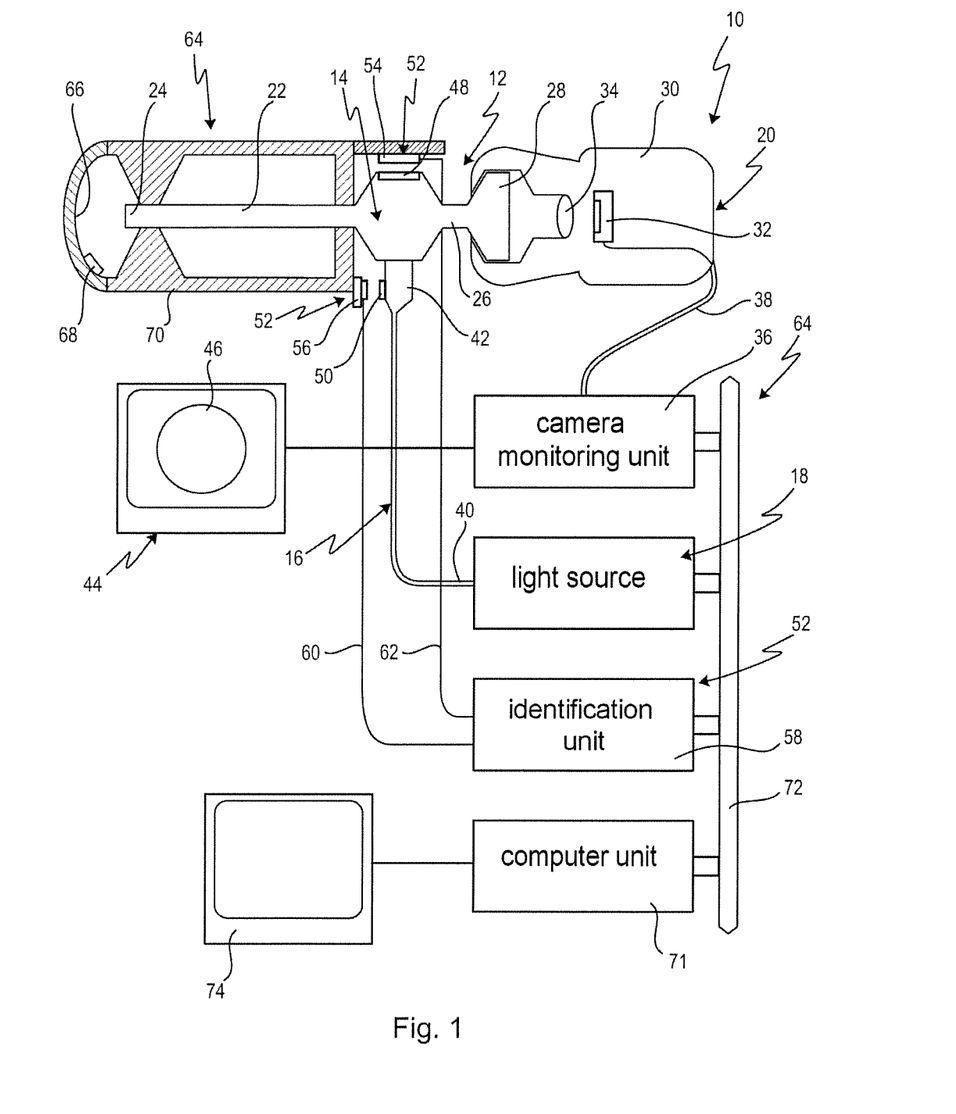
FIG. 1 shows an apparatus for examining the light and/or image transmission properties of an endoscopic system in a block diagram.

In FIG. 1, an apparatus, designated with the general reference number 10, for examining the light and/or image transmission properties of an endoscopic system 12 is shown. It is to be understood that the apparatus 10 is suitable also for examining the light and/or image transmission properties of an exoscopic system (not illustrated).

The endoscopic system 12 has among others the components endoscope 14, light carrier 16, light source 18 and camera 20. An exoscopic system correspondingly has, instead of the endoscope 14, an exoscope (not illustrated). The following description applies analogously to an exoscope in place of the endoscope 14.

The endoscope 14 has a shaft 22, which can be rigid or flexible. In the exemplary embodiment shown here, the endoscope 14 is a conventional endoscope in which the image transmission is carried out from a distal end 24 of the shaft 22 to a proximal end 26 of the shaft using glass fibres or a relay lens system. An eyepiece 28 is correspondingly arranged at the proximal end 26 of the shaft 22.

The camera 20 comprises an imager 32 arranged in a camera head 30 and an objective 34 and a camera control unit 36, which is connected to the imager 32 via a signal line 38 or a feed line.

In other exemplary embodiments (not illustrated), the endoscope 14 can also be a video endoscope in which the imager 32 is integrated in the endoscope 14 together with the objective 34. In this case, the components endoscope and camera (with the exclusion of the camera monitoring unit) are merged.

Furthermore, not only an image transmission section but also a light transmission section for transmitting light generated by the light source 18 extends in the endoscope 14 through the shaft 22 of the endoscope 14 toward the distal end 24 of the shaft 22 from which the light is emitted.

In the exemplary embodiment illustrated, the light carrier 16 is a light-guide cable which is connected by a proximal end 40 to the light source 18 and by a distal end 42 to the endoscope 14, wherein the light generated by the light source 18 is transmitted to the endoscope 14 via the light carrier 16.

In other exemplary embodiments (not illustrated), the light source can also be coupled directly to the endoscope 14 or be integrated therein, such that in this case the endoscope and the light carrier are merged into one component.

The endoscopic system 12 shown in FIG. 1 with the components endoscope 14, light carrier 16, light source 18 and camera 20 represents a current component combination, wherein the components are connected to one another to be ready for operation.

The endoscopic system 12 furthermore comprises, as a further component, a monitor 44, with which the endoscopic image 46 picked up by the endoscope 14 and the camera 20 can be visualized.

A clinic typically has a plurality of endoscopes 14 and a plurality of light carriers 16, typically also a plurality of cameras 20 and light sources 18, which can be combined in virtually any desired combination. For reasons of simplification, the following description assumes that the endoscope 14 and the light carrier 16 are taken from a supply quantity of endoscopes E1, . . . , En and light carriers L1, . . . , Lm (FIGS. 5 and 6), which are available in a clinic, while for each combination of endoscopes 14 and light carriers 16, the same camera 20 and the same light source 18 are used. However, it is to be understood that a plurality of cameras 20 and a plurality of light sources 18 are also used in various component combinations.

The endoscope 14 is provided with an identifier 48 which individualizes the current endoscope 14. The identifier 48 can be configured in the form of a chip or a transponder on which identification data is contained, such as for example the article and serial number of the current endoscope 14.

The light carrier 16 is likewise provided with an identifier 50 containing identification data that individualizes the current light carrier 16, wherein the identifier 50 may again be configured as a chip or a transponder. Using the identification data contained in the identifiers 48 and 50, the current endoscope 14 and the current light carrier 16 can be uniquely identified.

The apparatus 10 has an identification unit 52 which is able to capture the identification data of the endoscope 14 and of the light carrier 16. The identification unit 52 has to this end reading modules 54 and 56, which can contactlessly read the identification data contained in the identifiers 48 and 50, wherein any type of contactless auto ID technology can be used here. The reading modules 54 and 56 are connected to a control unit 58 of the identification unit via corresponding signal lines 60 and 62, although wireless transmission is also possible instead of signal lines.

The apparatus 10 furthermore has a measurement system 64, with which at least one transmission parameter of the current component combination of endoscope 14, light carrier 16, light source 18 and camera 20 can be captured. The measurement system 64 has a measurement target 66, which has for example a test image or simply a diffusely scattering surface. The measurement system 64 can furthermore have a measurement sensor 68, with which for example the light intensity emitted by the endoscope 14 can be directly measured. The measurement sensor 68 is in this case configured as a brightness sensor. The measurement system 64 furthermore has a measurement adapter 70, which can be fitted onto the shaft 22 of the endoscope 14. The measurement adapter 70 has, in the exemplary embodiment illustrated, the reading modules 54 and 56 of the identification unit 52 integrated therein.

A transmission parameter captured during the examination of the endoscopic system 12 can for example be the light intensity emitted by the endoscope 14, which can be measured for example via the measurement sensor 68. In addition or alternatively, it is also possible for the image brightness of the image of the measurement target 66, which is transmitted from the endoscope 14 via the objective 34 onto the imager 32 and is picked up thereby, to be captured by the camera control unit 36 or a corresponding device within the monitor 44.

To this extent, the camera 20 can likewise be part of the measurement system 64.

The apparatus 10 furthermore has a computer unit 71 which is connected to the identification unit 52 (in this case the control unit 58), the light source 18 and the camera 20 (in this case the camera control unit 36) via a bus 72 (for example the KARL STORZ SCB bus from Karl Storz GmbH & Co. KG).

The measurement sensor 68 is likewise connected to the computer unit 71 in order to transmit captured measurement values to the computer unit 71. In the exemplary embodiment illustrated, the connection is wireless.

The computer unit 71 is furthermore connected to an output device 74, for example a monitor, for visually representing the result of the examination of the endoscopic system 12.

The camera 20 and the light source 18 also have a unique identification feature, for example by way of their article and serial number, which can be stored as an identifier in a memory element in the device and which is read by the computer unit 71 during an examination of the endoscopic system 12. In addition, it is possible not only for the device identification data, but also for set operating parameters of the camera 20 and the light source 18 to be readout by the computer unit 71 via the bus 72. Furthermore, it is also possible via the computer unit 71 to set different operating parameters of the camera 20 and the light source 18.

Figure 2:
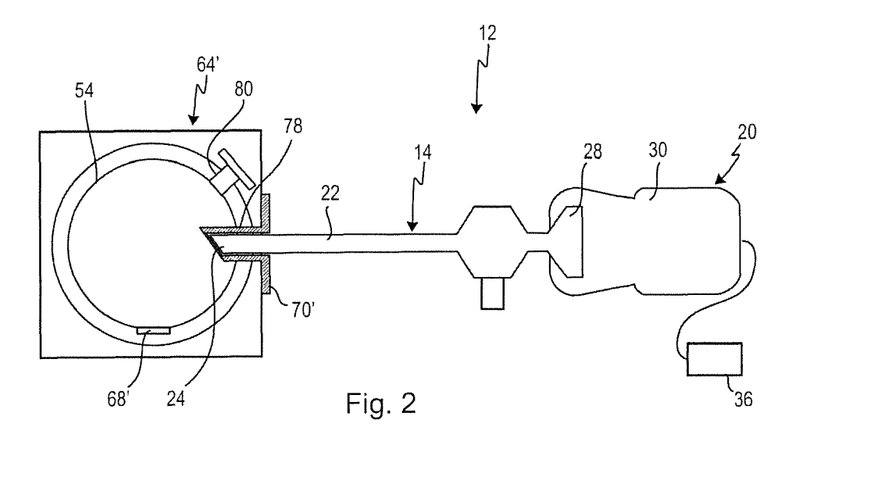
FIG. 2 shows a part of an apparatus for examining the light and/or image transmission properties of an endoscopic system with a measurement system that differs from that in FIG. 1.

FIG. 2 shows the endoscopic system 12 only in the framework of the endoscope 14 and the camera 20, wherein the exemplary embodiment in FIG. 2 shows a measurement system 64' which is modified with respect to the measurement system 64 in FIG. 1. The measurement system 64' has in this case an Ulbricht sphere 76 which diffusely scatters light emitted by the endoscope 14. The Ulbricht sphere 76 furthermore has a measurement sensor 68', which is comparable to the measurement sensor 68 in FIG. 1. The measurement system 64' here has a plurality of coupling openings 78 and 80, with the coupling opening 78 serving for coupling the endoscope 14, and the coupling opening 80 serving for coupling the light carrier 16 (not shown in FIG. 2). It is thus possible to carry out individual examination of the light carrier 16 and light source 18 without the endoscope 14. The endoscope 14 is here shown in an oblique view, as compared to FIG. 1, wherein the viewing direction of the endoscope 14 is 30° with respect to the longitudinal axis of the shaft 22 of the endoscope 14. However, this is only one example of a possible viewing direction of endoscopes.

Figure 3A:
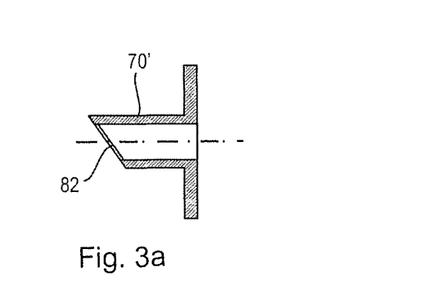
FIGS. 3a) and b) in each case show an exemplary embodiment of a measurement adapter for use in the measurement system in FIG. 2.

The measurement system 64' here has a measurement adapter 70', which is shown by itself in FIG. 3a). The measurement adapter 70' can be inserted into the coupling opening 78. The measurement adapter 70' is matched to the respective current endoscope 14, wherein different embodiments of measurement adapters can be kept ready for different types of endoscopes 14. The measurement adapter 70' ensures for its part a defined distance between the distal end 24 of the shaft 22 and the measurement target, in this case the internal surface of the Ulbricht sphere 76, and protects the cleaned endoscope 14 against premature contamination by way of sterile designs.

However, it is likewise conceivable that the measurement system 64 or 64' overall is designed as a sterile disposable product or in sterilizable form.

Figure 3B:
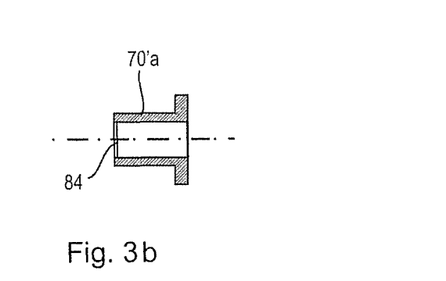
Figure 4:
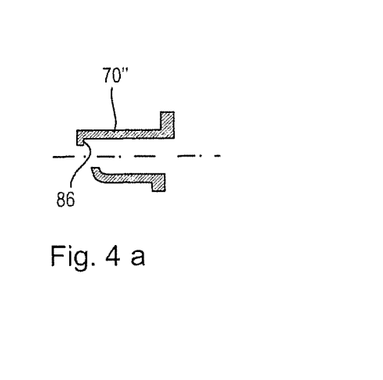

The measurement adapter 70' has at its distal end a membrane 82, which is transparent and here ensures a defined insertion depth of the shaft 22 of the endoscope 14 into the measurement adapter 70'. FIG. 3b) shows a measurement adapter 70'a with a membrane 84 for an endoscope 14 with a straight-ahead viewing direction, as is shown in FIG. 1. FIG. 4a) shows a measurement adapter 70", which is designed without a membrane, in contrast to the measurement adapter 70' in FIG. 3a), but instead has a flange 86 as an abutment for the distal end 24 of the shaft 22 of the endoscope 14. While the measurement adapter 70" in FIG. 4a) is configured for an endoscope 14 with oblique viewing optics, a measurement adapter 70"a shown in FIG. 4b) for an endoscope 14 is configured with a straight-ahead viewing direction, as shown in FIG. 1. The measurement adapter 70"a likewise has at its distal end a flange 88 as an abutment for the distal end 24 of the shaft 22 of the endoscope 14.

Again with reference to FIG. 1, a method for examining the light and/or image transmission properties of the endoscopic system 12 is described below. In the examination of a current combination of the components endoscope 14, light carrier 16, light source 18 and camera 20, first the endoscope 14 is coupled to the measurement system 64 via the measurement adapter 70. Thereafter, the identification data of the endoscope 14 and of the light carrier 16 are readout by the reading modules 54, 56 from the identifiers 48 and 50. In addition, a transmission parameter of the current component combination, for example the transmitted light output, light intensity and so on, which makes statements regarding the performance of the current component combination as a whole, is captured. In one concrete example, the intensity of the image of the reference (measurement target 66), as is captured by the camera 20, can be used as such a transmission parameter. In addition, the identification data is readout from the camera 20 and the light source 18, as are the set operating parameters of the camera 20 and the light source 18.

The captured transmission parameter or parameters, the identification data captured by the identification unit 52 of the endoscope 14 and of the light carrier 16, the operating parameters set in the camera 20 and the light source 18 and the identification data thereof are stored in the computer unit 71 in a memory unit thereof.

The computer unit 71 contains an evaluation unit, which evaluates the currently captured transmission parameter so as to ascertain the operational capability of the current component combination of endoscope 14, light carrier 16, light source 18 and camera 20 for use in a subsequent surgical procedure, wherein the result of said evaluation is also stored in the computer unit 71. The previously mentioned evaluation is carried out by comparing the transmission parameter or parameters with a nominal value or values.

The result of the evaluation, which contains a statement regarding the current operational capability of the current component combination, can be displayed to the clinic personnel involved in the carrying out of the examination on the output device 74, for example via a traffic light representation (red/amber/green).

In each examination of a current component combination, it should be ensured that the operating parameters zoom and focus of the camera 20 have identical settings across the objective 34 of the camera 20 from one examination to the next. Zoom and focus of the camera 20 can be readout, as already described above, by the computer unit 71 via the bus 72 from the camera 20 and set. The set zoom and focus can, however, also be ascertained by way of the size of the endoscopic image 46 on the monitor 44. The images of endoscopes generally have a centric circle section, the size of which depends on the set zoom factor. If the focus and zoom of the current camera 20 cannot be set by way of a motor, but only manually, it is therefore alternatively also possible, based on the knowledge of the endoscope and camera type, to determine the magnification factor set at the time of the examination by way of reference to an image analysis of the image 46.

It is furthermore advantageous if a timestamp is also stored for each examination carried out of a current component combination.

In the method according to the invention, the endoscopic system 12 is examined as a whole, as described above. The method according to the invention, however, makes it advantageously possible to make statements regarding the performance of specific individual components, such as for example a specific endoscope 14 or a specific light carrier 16 or a specific light source 18 or a specific camera 20, from examinations of various component combinations that are carried out at time intervals, without said components requiring individual examination. This is described in more detail below.

The endoscopic total transfer function H(f) with respect to the light transmittance can be represented as a product of the individual transfer functions of the components $H_i(f)$:

$$H(f) = \prod_{i=1}^{n} H_i(f)$$

In approximation it should be assumed that the transmission properties of the individual components in the visible wavelength range are constant, that is to say the transfer functions of the components can be described by the transmission coefficient $T_i$ of the components:

$$T_g = \prod_{i=1}^{n} T_i$$

$T_g$ is the total transmittance. It should furthermore be assumed that with a constant distance between endoscope 14 and measurement target 66 and with a constant reflection, the transmission from the endoscope 14 to the measurement target 66 and back to the endoscope corresponds to a constant $T_r$.

Relevant for the change in the transmission behavior are now the transmittances of the respective endoscope 14, the respective light carrier 16, the respective light source 18 and the respective camera 20.

According to experience, the components light carrier 16 and endoscope 14 exhibit a degradation which increases over time, i.e. the transmittance thereof diminishes over time, owing to the processing of said components in an autoclave.

For the component light source 18, a reduction in the luminance is primarily dependent on the luminous medium. While in semiconductor-based luminous means, such as for example LEDs, a very long operating time is achieved with constant luminance, high-pressure short-arc lamps, for example on xenon basis, degrade relatively quickly owing to the increasing electrode spacing on account of their ignition.

Cameras such as the camera 20 have, according to experience, a transmittance which is constant over time. As already mentioned, however, for each examination zoom and focus must be set to be identical across the camera lens 34, because only in this case a constant transmittance (ratio of incident light to intensity of the electrical signal of the camera) can be assumed. A degradation of the camera 20 over time, however, should be assumed if the camera head 30 is also sterilized or autoclaved.

Figure 5:
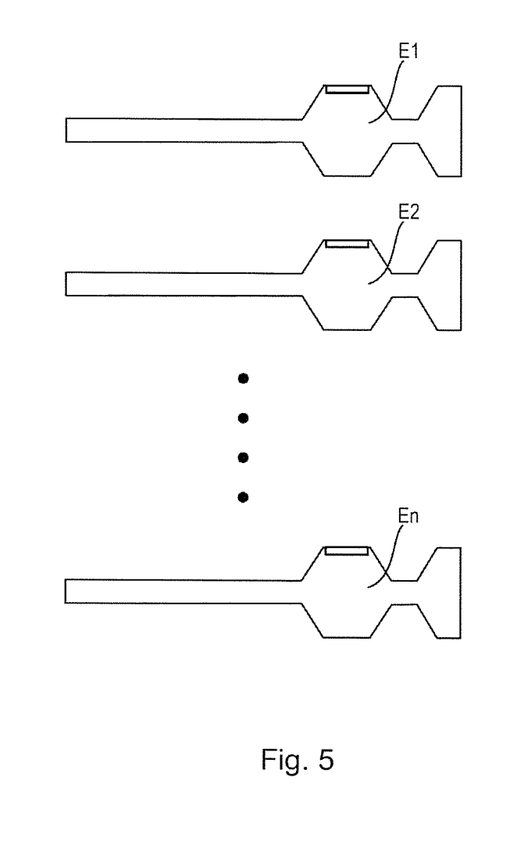
FIG. 5 shows a supply quantity of endoscopes for use in an endoscopic system.
Figure 6:
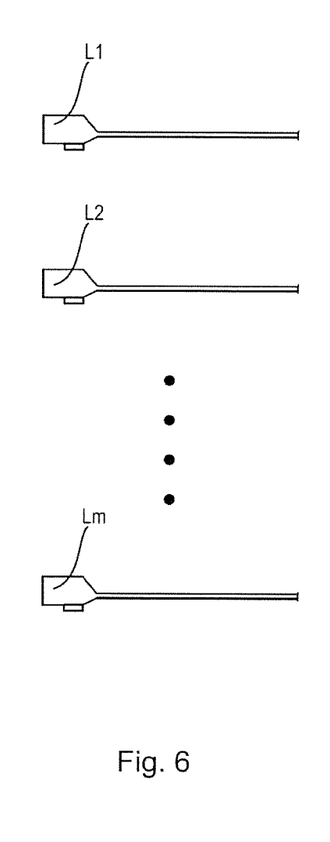
FIG. 6 shows a supply quantity of light carriers for use in an endoscopic system.

A clinic typically has a supply quantity of endoscopes E1, . . . , En, as shown in FIG. 5, and a supply quantity of light carriers L1, . . . , Lm, as shown in FIG. 6. The reason for this is that for each use of an endoscope and of a light guide in a surgical procedure, the endoscope and light guide must be reconditioned. So as to ensure uninhibited process of the surgical procedure and thus optimum use of the operating room without downtimes due to reconditioning, clinics nowadays have a correspondingly large number of endoscopes and light guides.

For a corresponding number of endoscopes E1, . . . , En and light carriers L1, . . . , Lm, in statistical terms, different endoscope/light guide combinations are used. In the example described below for a statistical evaluation of examinations that are carried out at time intervals of the light and/or image transmission properties of different component combinations, it is assumed for the sake of simplicity that in a clinic five endoscopes E1, . . . , E5, five light carriers L1, . . . , L5, one camera K1 and one light source LQ1 are present. The principle of the statistical evaluation to be described below can of course also be applied to a greater number of endoscopes, light carriers, cameras and light sources.

Figure 7:
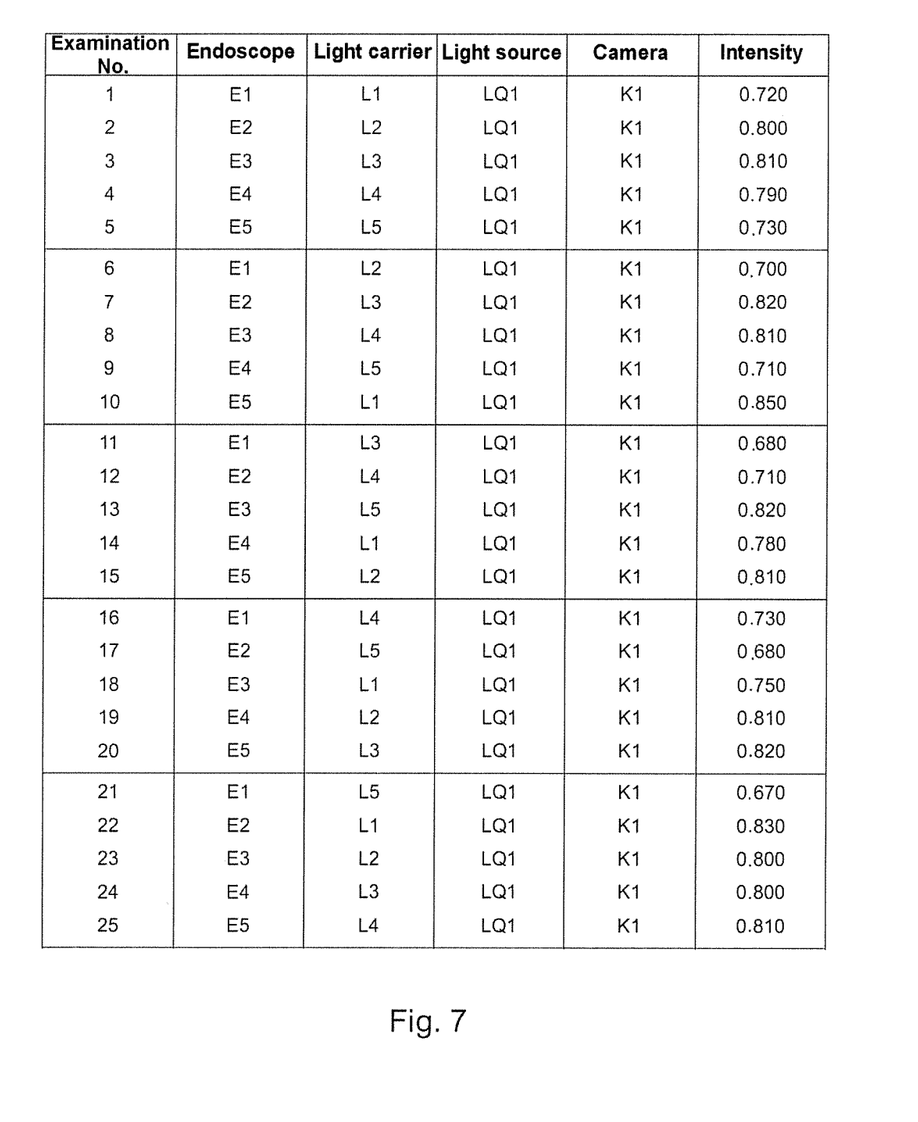
FIG. 7 shows a table in which, by way of example, results from temporally sequential examinations of 25 different component combinations of endoscopic systems are listed in the form of examples.

FIG. 7 lists an example of 25 examinations of different component combinations of the endoscopes E1 to E5, the light carriers L1 to L5, the light source LQ1 and the camera K1 in the form of a table. In examination No. 1, the component combination E1, L1, LQ1, K1 as a whole is measured, in the examination No. 2 the component combination E2, L2, LQ1, K1 as a whole is measured, and so on.

In each examination of the concrete component combination as a whole, the transmission parameter that was captured was the overall intensity, that is to say the intensity that can still be measured owing to the transmittance over all components involved. The intensity measured in each case during the examinations of the corresponding component combinations is listed in the last column in the table in FIG. 7. The intensity is here given without dimension.

For each examination of the current component combination, the captured transmission parameters (in this case intensities) were stored in the memory unit of the computer unit 71 (FIG. 1). The number of stored transmission parameters which are stored together with the identification data of the components involved thus successively increases over time, as a result of which a retrospective statistical evaluation becomes possible. The computer unit 71 contains a program that evaluates the stored transmission parameters (the intensities in the present case) as to the performance of individual components, in this case the endoscopes E1 to E5 and light guides L1 to L5.

The way in which such an evaluation can take place is described with reference to FIG. 8.

Figure 8:
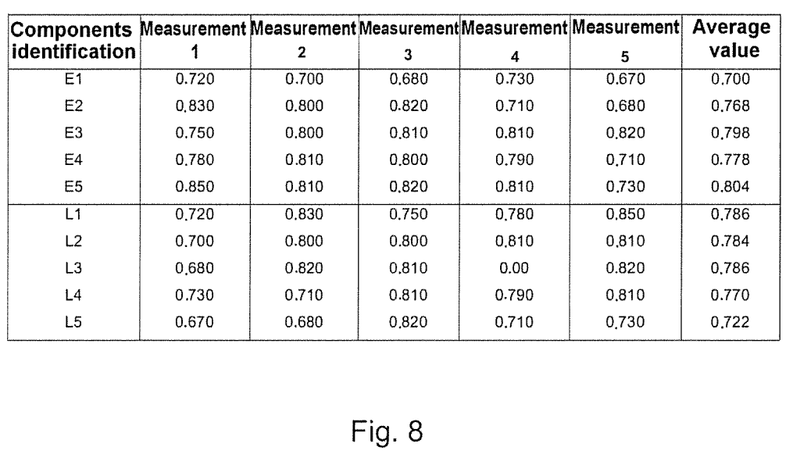
FIG. 8 shows a further table in which, by way of example, a statistical evaluation of the examination results in FIG. 7 is illustrated with respect to the performance of the endoscopes and light carriers used in the examined component combinations.

FIG. 8 lists the transmission parameters captured during the examinations according to FIG. 7 of those component combinations in which the respective endoscope E1 to E5 and the respective light guide L1 to L5 were involved. Owing to the storing of the identification data of the respective endoscope E1, . . . , E5 and of the respective light carrier L1, . . . , L5 for each examination together with the captured transmission parameters of the respective overall system, a unique assignment of captured transmission parameters of the respectively total component combination to the endoscope or light carrier which were involved in the respective component combination even at a time after the examination is possible. The endoscope E1 can be uniquely assigned the captured transmission parameters of the examination No. 1 ("measurement 1"), the examination No. 6 ("measurement 2"), the examination No. 11 ("measurement 3"), the examination No. 16 ("measurement 4") and the examination No. 21 ("measurement 5") in FIG. 7, the light guide L1 can be uniquely assigned the captured transmission parameters of the examination No. 1 ("measurement 1), the examination No. 10 ("measurement 2"), the examination No. 14 ("measurement 3"), the examination No. 18 ("measurement 4") and the examination No. 22 ("measurement 5") in FIG. 7, and so on. For each component E1 to E5 and L1 to L5, the statistical evaluation of the captured transmission parameters are carried out by way of averaging which is given in the last column in the table in FIG. 8. The lowest average for the endoscopes E1 to E5 can then be used to deduce the worst one of the endoscopes E1 to E5. In the present example, this is endoscope E1. The evaluation for the light carriers L1 to L5 is carried out analogously, wherein in the present example the light guide L5 can be selected as the worst light guide.

It is to be understood that the evaluation algorithm is not dependent on the number of endoscopes and the number of light guides being identical, as in the present example, but they can be different. Likewise, the evaluation can be carried out if more than just one light source of more than just one camera are involved in the various component combinations.

The above-mentioned evaluation of the transmission parameters recorded sequentially over time of different component combinations is carried out after a certain number of measurements with a specific component according to the principle of the "limited memory" or according to the principle of the "diminishing memory". In the example of FIG. 8, the principle of "limited memory" was used.

In the principle of "limited memory", captured transmission parameters from measurements which were taken earlier are not taken into account any more:

$$u(k) = \frac{1}{N} \sum_{i=k-N+1}^{k} y(i)$$

with the recursion formula:

$$u(k) = u(k-1) + \frac{1}{N}[y(k) - y(k-N)],$$

wherein N is the number of measurements taken into account. y(i) is the transmission parameter captured in the i-th measurement, in which a specific component was involved. In the example of FIG. 8 N=5.

According to the principle of the "diminishing memory", captured transmission parameters from measurements which were taken increasingly earlier are given a decreasing weighting:

The recursion formula:

$$u(k)=\lambda \cdot u(k-1)+(1-\lambda)y(k),$$

applies, wherein λ is a weighting factor with a magnitude of less than 1. If the weighting factor λ approaches zero, the transmission parameters from more recent or current measurements receive an increasingly stronger weighting.

Since the captured transmission parameters deteriorate over time owing to the degradation of individual components, in particular of endoscopes and light guides, i.e. become "worse", the underlying process is "slow time invariant" and requires that captured transmission parameters from measurements taken earlier are not at all weighted and/or are weighted lower than current ones.

The above stated formula can be applied either to the number of examinations carried out of component combinations or to the number of measurements carried out in which the same component was involved. In the previously described exemplary embodiment of FIGS. 7 and 8, the formulae were applied to the number of measurements carried out, such that N=5 (measurements 1 to 5) should be used.

The examination, described above with reference to FIG. 1, of the current component combination of endoscope 14, light carrier 16, light source 18 and camera 20 is preferably carried out immediately before the use of the component combination in a surgical procedure. However, it is to be understood that the examination can also be carried out after the use of the current component combination in a surgical procedure.

It is likewise possible to carry out the examination method, that is the examination of the current component combination, during the use of said combination in a surgical procedure, wherein not the measurement target 66 with the measurement adapter 70 is used as the measurement target, but an area of tissue or an instrument at the intracorporeal site is used as a measurement target. Such an instrument at the intracorporeal site can be for example the trocar sleeve, through which the endoscope 14 is inserted into the operating site. In the case that the examination method is carried out during the surgical procedure, preferably a multiplicity of individual examinations is carried out, wherein at least those results from the individual examinations are stored that represent a poor state of the current component combination.

Since during an examination in the operating site the captured transmission parameter has a significantly larger variance in different tissues surfaces, this is taken into account by a multiplicity of individual examinations being carried out. While the examination method in the operating site is carried out, the image brightness in the endoscopic image of the camera 20 is captured as the transmission parameter, wherein the image brightness is determined by the exposure time, the amplification and the average intensity value (luminance) in a predetermined region of interest in the endoscopic image of the camera.

While the above-described evaluations of the examinations can be carried out with respect to the operational capability of the current component combination as a whole and the evaluation of successive examinations can be carried out with respect to the performance of individual components of the endoscopic system in the computer unit 71, it is likewise possible for the computer unit 71 to transmit the captured data, in particular identification data, transmission parameters and possibly operating parameters, to a remote computer unit for evaluation therein, for example in a service operation, for example at the manufacturer of the components of endoscopic systems. From there, it is possible to furnish the relevant clinic with indications relating to any poor states of individual components or to imminent degradations.

The invention claimed is:

1. A method, comprising:
    providing an endoscopic or exoscopic system having the components: an endoscope or exoscope, a light-guide cable, a light source and a camera, wherein the light-guide cable is configured to connect the light source to the endoscope or exoscope,
        wherein the following is met:
            the endoscope/exoscope is taken from a first supply quantity of endoscopes or exoscopes, wherein the endoscope/exoscope is provided with an endoscope/exoscope identifier containing endoscope/exoscope identification data individualizing the endoscope/exoscope;
            the light-guide cable is taken from a second supply quantity of light-guide cables, wherein the light-guide cable is provided with a light-guide cable identifier containing light-guide cable identification data individualizing the light-guide cable;
        wherein the endoscope/exoscope, the light-guide cable, the light source and the camera are connected to each other so as to be ready for surgical operation in the form of a component combination; and
        wherein the light-guide cable is removably connected to the endoscope/exoscope;
    further comprising examining at least one of a light transmission quality and an image transmission quality of the endoscopic or exoscopic system, the examining including:
        capturing the endoscope/exoscope identification data and the light-guide cable identification data;
        measuring a transmission quality parameter of the component combination;
        storing in a memory the endoscope/exoscope identification data, the light-guide cable identification data, and the measured transmission quality parameter;
        repeatedly performing the series of steps above, taking different endoscope/exoscopes from the first supply quantity of endoscopes or exoscopes, and/or taking different light-guide cables from the second supply quantity of light-guide cables, so as to provide different component combinations;
        evaluating the respective transmission quality parameters of the different component combinations stored in the memory; and
        deducing a performance quality of an individual component included in at least one of the different component combinations, based on the evaluation of the respective transmission qualities of the different component combinations.

2. The method of claim 1, wherein the repeated series of steps further includes evaluating the transmission quality parameter so as to ascertain an operational capability of the component combination for use in a surgical procedure.

3. The method of claim 2, wherein the step of evaluating the transmission quality parameter includes comparing the transmission quality parameter to a nominal value.

4. The method of claim 1, wherein the repeated series of steps further includes reading out at least one of light source identification data of the light source and a camera operating parameter of the camera.

5. The method of claim 4, wherein the repeated series of steps further includes setting the camera operating parameter.

6. The method of claim 4, wherein the repeated series of steps further includes setting a light source operating parameter of the light source.

7. The method of claim 1, wherein the repeated series of steps further includes analyzing an image supplied by the component combination so as to ascertain a current setting of an operating parameter of the camera of the component combination.

8. The method of claim 1, wherein the repeated series of steps further includes storing a timestamp in addition to the storing of the endoscope/exoscope identification data and the light-guide cable identification data and to the storing of the measured transmission quality parameter.

9. The method of claim 1, further comprising carrying out the evaluating with a weighting such that stored transmission quality parameters that were measured earlier have a lower weighting than stored transmission quality parameters which are measured later, or are not taken into consideration.

10. The method of claim 1, wherein the repeated series of steps further includes carrying out the examination of the component combination before use of the component combination in a surgical procedure.

11. The method of claim 10, wherein the repeated series of steps further includes carrying out the examination of the component combination using at least one of a measurement target and a measurement sensor connected to the endoscope/exoscope.

12. The method of claim 1, wherein the repeated series of steps further includes carrying out the examination of the component combination during use of the component combination in a surgical procedure, wherein at least one of an area of tissue and an instrument at the intracorporeal site is used as a measurement target.

13. The method of claim 12, wherein the repeated series of steps further includes carrying out a multiplicity of individual examinations during the surgical procedure, and storing at least those results from individual examinations that represent a poor-quality state of the component combination.

14. The method of claim 13, further comprising capturing an incidence of occurrence of the captured poor-quality states.

15. An apparatus, comprising:
    an endoscopic or exoscopic system having the components: an endoscope or exoscope, a light-guide cable, a light source and a camera, wherein the following is met:
        the endoscope/exoscope is taken from a first supply quantity of endoscopes or exoscopes, wherein the endoscope/exoscope is provided with an endoscope/ exoscope identifier containing endoscope/exoscope identification data individualizing the endoscope/exoscope;

the light-guide cable is taken from a second supply quantity of light-guide cables, wherein the light-guide cable is provided with a light-guide cable identifier containing light-guide cable identification data individualizing the light-guide cable;

wherein the endoscope/exoscope, the light-guide cable, the light source and the camera are connected to each other so as to be ready for operation in the form of a component combination; and wherein the light-guide cable is removably connected to the endoscope/exoscope;

the apparatus further comprising:

an identifier which captures the endoscope/exoscope identification data and the light-guide cable identification data;

a measurement system that measures a transmission quality parameter of the component combination; and a computer to which the measurement system and the identifier are connected and which has a memory for storing the endoscope/exoscope identification data and the light-guide cable identification data and for storing the measured transmission quality parameter of the component combination;

wherein respective transmission quality parameters of a plurality of different component combinations are stored in the memory, further comprising a program that evaluates the respective transmission quality parameters of the plurality of different component combinations in terms of a performance of individual components.

16. The apparatus of claim 15, wherein the computer has an evaluator, which evaluates the transmission quality parameter currently measured so as to ascertain an operational capability of the current component combination for use in a surgical procedure.

17. The apparatus of claim 16, wherein the evaluator compares the transmission quality parameter currently measured to a nominal value.

18. The apparatus of claim 15, wherein the program contains an algorithm which in the evaluation of the transmission quality parameters does not take into consideration transmission quality parameters that were measured earlier or gives transmission quality parameters that were measured earlier a lower weighting than transmission quality parameters that were measured later.

19. The apparatus of claim 15, wherein at least one of the camera and the light source is networked with the computer such that at least one of camera identification data, a camera operating parameter of the camera, light source identification data and a light source operating parameter of the light source can be readout into the computer.

20. The apparatus of claim 19, wherein at least one of the camera operating parameter and the light source operating parameter is set via the computer.

21. The apparatus of claim 15, wherein the computer has an image analysis device.

22. The apparatus of claim 15, wherein the computer is configured for transmitting the captured endoscope/exoscope identification data and transmission quality parameter to a remote computer for evaluation.

23. The apparatus of claim 15, wherein the measurement system has at least one coupling opening for coupling at least one of the endoscope/exoscope and the light-guide cable.

24. The apparatus of claim 15, wherein the measurement system has at least one of a measurement target and a measurement sensor.

25. The apparatus of claim 24, wherein the measurement system has a measurement adapter, via which the endoscope/exoscope can be coupled to the measurement system such that the distance of a distal end of the endoscope/exoscope to the measurement target is well-defined.

26. The apparatus of claim 15, wherein at least one of the endoscope/exoscope identifier and the light-guide cable identifier cooperates with the identifier contactlessly.

27. The method of claim 1, wherein the transmission quality parameter is at least one of a light intensity of light emitted by the endoscope/exoscope and an image brightness of an image captured by the camera.

28. A method, comprising:

selecting an imaging scope from a supply quantity of imaging scopes;

selecting a light-guide cable from a supply quantity of light-guide cables;

providing a component combination ready for surgical operation and having: a camera, a light source, the selected imaging scope, and the selected light-guide cable connecting the light source to the selected imaging scope, wherein the selected light-guide cable is removably connected to the selected imaging scope;

capturing individualizing ID data from the selected imaging scope;

capturing individualizing ID data from the selected light-guide cable;

measuring a transmission quality parameter of the component combination;

storing the measured transmission quality parameter of the component combination, and the individualizing ID data captured from the selected imaging scope and the selected light-guide cable;

repeatedly performing the series of steps above, selecting different imaging scopes from the supply quantity of imaging scopes, and/or selecting different light-guide cables from the supply quantity of light-guide cables, so as to provide different component combinations;

evaluating the respective transmission quality parameters of the different component combinations, and thereby deducing a performance of an individual component included in at least one of the different component combinations.

29. The method of claim 28, wherein the selected imaging scope is an endoscope or an exoscope.

* * * * *